United States Patent
Casaubon Seignour et al.

(10) Patent No.: US 7,183,449 B2
(45) Date of Patent: Feb. 27, 2007

(54) PROCESS FOR THE TREATMENT OF THE BY-PRODUCTS FROM A REACTION FOR THE PRODUCTION OF ORGANIC COMPOUNDS

(75) Inventors: Lionel Casaubon Seignour, Tavaux (FR); Philippe Krafft, Tavaux (FR); Bruno Fouchet, Tavaux (FR)

(73) Assignee: Solvay S.A., Brussels (BE)

( * ) Notice: Subject to any disclaimer, the term of this patent is extended or adjusted under 35 U.S.C. 154(b) by 427 days.

(21) Appl. No.: 10/481,661

(22) PCT Filed: Jun. 21, 2002

(86) PCT No.: PCT/EP02/07001

§ 371 (c)(1),
(2), (4) Date: Dec. 18, 2003

(87) PCT Pub. No.: WO03/000626

PCT Pub. Date: Jan. 3, 2003

(65) Prior Publication Data

US 2004/0194258 A1    Oct. 7, 2004

(30) Foreign Application Priority Data

Jun. 22, 2001 (FR) .................................. 01 08374

(51) Int. Cl.
*C07C 17/38* (2006.01)
*C07C 17/20* (2006.01)
(52) U.S. Cl. ...................... 570/177; 570/170
(58) Field of Classification Search ............... 570/177, 570/178, 170
See application file for complete search history.

(56) References Cited

U.S. PATENT DOCUMENTS

| | | | | |
|---|---|---|---|---|
| 2,678,954 A | * | 5/1954 | O'Neil et al. ............ | 208/262.1 |
| 4,168,283 A | | 9/1979 | Beilstein et al. | |
| 5,169,533 A | * | 12/1992 | Baker et al. ................ | 210/640 |
| 5,853,550 A | * | 12/1998 | Landers et al. ............... | 203/29 |

FOREIGN PATENT DOCUMENTS

| | | |
|---|---|---|
| EP | 0098341 | 1/1984 |
| JP | 62197101 A | 8/1987 |
| SU | 0821441 | 4/1981 |
| SU | 0952833 | 8/1998 |
| WO | WO-97/38959 | 10/1997 |

OTHER PUBLICATIONS

Derwent Abstract of AN-1982-07500E [04], XP-002191955 (Berlin E R).
Derwent Abstract of AN-1983-703955 [27], XP-002191954 (Manlulo A P).
Derwent Abstract of AN-1987-281777 [40], XP-002191956 (Mitsui Toatsu Chem. Inc.).

* cited by examiner

*Primary Examiner*—J. Parsa
(74) *Attorney, Agent, or Firm*—Connolly Bove Lodge & Hutz LLP

(57) ABSTRACT

Process for the treatment of by-products from a reaction for the production of organic compounds comprising a stage of evaporation of a liquid phase comprising heavy by-products on a surface, in order to form a concentrated phase comprising the bulk of the heavy by-products and a vapor phase essentially devoid of heavy by-products, and a stage of recovery of the solid phase from the surface.

19 Claims, 1 Drawing Sheet

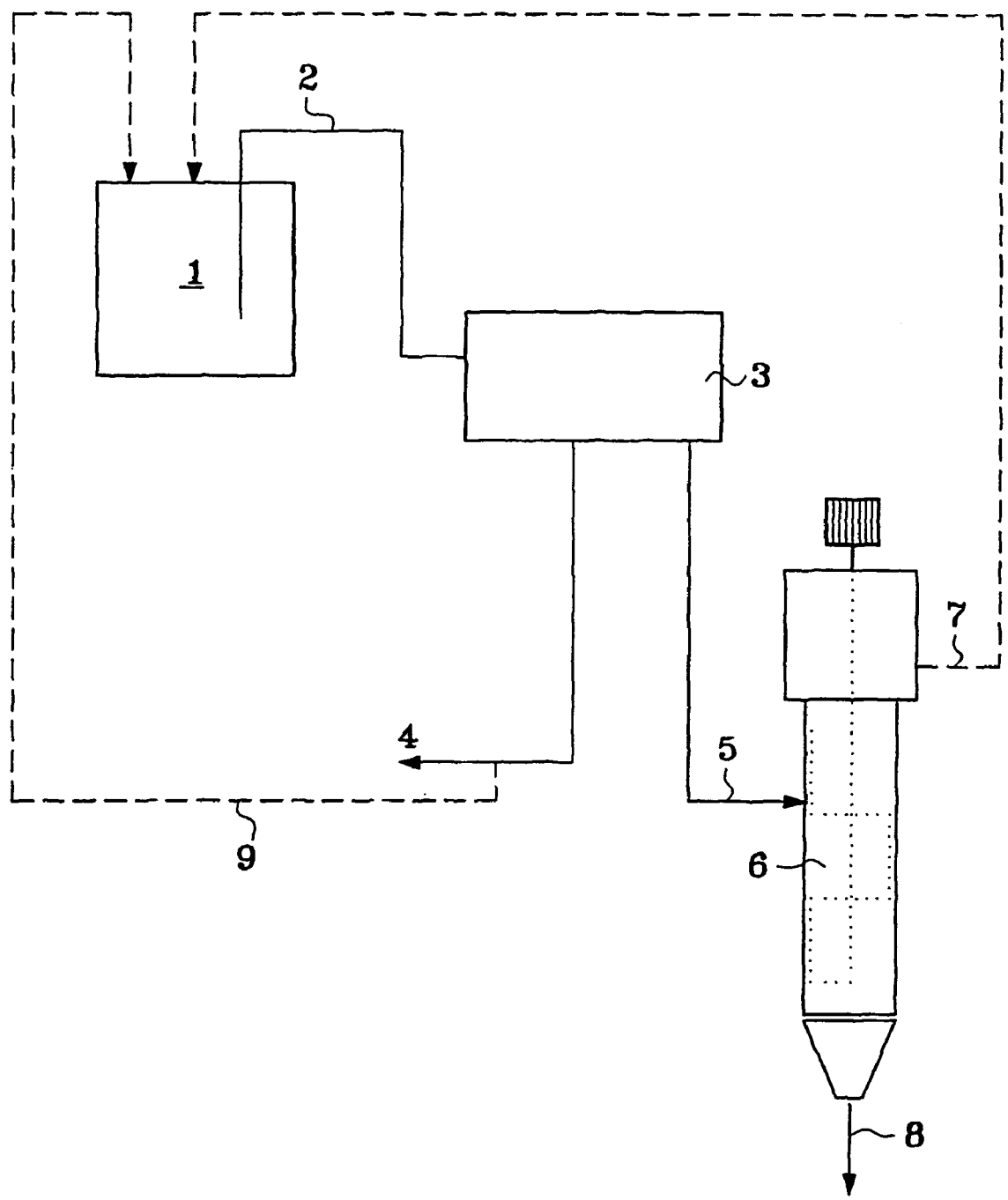

PROCESS FOR THE TREATMENT OF THE BY-PRODUCTS FROM A REACTION FOR THE PRODUCTION OF ORGANIC COMPOUNDS

The present invention relates to a process for the treatment of the by-products from a reaction for the production of organic compounds which can be used to remove by-products from an industrial reaction for the production of organic compounds.

In reactions for the production of organic compounds in the liquid phase, a problem usually encountered consists of the formation of heavy by-products which exhibit a boiling point greater than that of the reactants and solvents employed. This problem arises in particular during the manufacture of fluorinated compounds by reaction of an appropriate precursor with hydrogen fluoride. The formation of such by-products can be explained, for example, by oligomerization or polymerization reactions of organic materials present in the reaction medium. Furthermore, optionally, inorganic by-products, such as, for example, deactivated catalyst residues, also form part of the heavy by-products. The presence of heavy by-products is unfavourable to the progression of the reaction for the production of an organic compound and thus it is necessary to remove them from the reaction medium. Industrially, bleeding operations are regularly carried out on the reaction medium for this purpose.

The by-products subsequently have to be treated in order to recycle a maximum amount of reactants to the reaction for the production of the organic compound and in order to provide for safe and environmentally-friendly destruction of the nonrecyclable waste.

Patent Application WO-A-97/38959 relates to a process for the treatment of the by-products from the reaction of organic compounds with anhydrous hydrogen fluoride. The by-products are concentrated by distillation and are subjected to extractive distillation with a saturated halogenated hydrocarbon. According to this known process, use is made, as extraction solvent, of halogenated hydrocarbons which can give rise to the formation of additional by-products under the conditions of the extractive distillation. The extraction solvent and the possible by-products have to be separated from the hydrogen fluoride before recycling it to the reactor. Large amounts of extraction solvent are consumed in dissolving the heavy by-products.

The invention is targeted at overcoming these problems.

The invention consequently relates to a process for the treatment of by-products from a reaction for the production of organic compounds comprising a stage of evaporation of a liquid phase comprising heavy by-products on a surface, in order to form a concentrated phase comprising the bulk of the heavy by-products and a vapour phase essentially devoid of heavy by-products, and a stage of recovery of the concentrated phase from the surface.

The process according to the invention applies to the treatment of by-products from reactions for the production of organic compounds carried out in the presence or in the absence of catalyst. Preferably, the process applies to by-products from a reaction catalysed by a metal derivative, in particular a metal salt. The metal derivative is advantageously chosen from the derivatives of the metals from Groups 3, 4, 5, 6, 13, 14 and 15 of the Periodic Table of the Elements (IUPAC 1988) and their mixtures (groups of the Periodic Table of the Elements formerly denoted IIIa, IIIb, IVa, IVb, Va, Vb and VIb). The term "derivatives of the metals" is understood to mean, inter alia, the hydroxides, the oxides and the organic and inorganic salts of these metals, and their mixtures. The process applies particularly to the by-products from a reaction catalysed by titanium, tantalum, molybdenum, boron, tin, antimony, chromium or zirconium derivatives, preferably catalysed by derivatives of the metals from Groups 4 (IVb), 14 (IVa) or 15 (Va) of the Periodic Table of the Elements and more particularly by titanium, tin or antimony derivatives. The process applies particularly to the by-products from a reaction catalysed by metal salts as metal derivative and these are preferably chosen from halides and more particularly from chlorides, fluorides and chlorides/fluorides. The process applies in a more particularly preferred way to the by-products from a reaction catalysed by titanium, tin or antimony chlorides, fluorides or chlorides/fluorides, in particular titanium tetrachloride, tin tetrachloride or antimony pentachloride. The process applies in a more particularly preferred way to the by-products from a reaction catalysed by tin tetrachloride.

When the process according to the invention is applied to the by-products from a reaction catalysed by a metal derivative, the concentrated phase generally comprises at least 5% by weight of metal. The content of metal is often at least 10% by weight. Preferably, this content is greater than or equal to approximately 20% by weight. This content often does not exceed 50% by weight.

The process according to the invention preferably applies to the treatment of the by-products from reactions for the production of organic compounds carried out in the liquid phase.

The process according to the invention preferably applies to the treatment of the by-products from reactions for the production of halogenated organic compounds. The halogenated organic compound often corresponds to the general formula

$$C_aH_bF_cCl_d \qquad (I)$$

in which a is an integer having the value 1, 2, 3, 4, 5, 6, 7, 8, 9 or 10, b is an integer having a value from 0 to 2a+1, c is an integer having a value from 0 to 2a+2, d is an integer having a value from 0 to 2a+2 and at least c or d is other than 0. Preferably, a is an integer having the value 1, 2, 3, 4 or 5.

The organic compound is preferably a fluorinated organic compound. Mention may in particular be made, among fluorinated organic compounds, of a hydrofluoroalkane chosen from difluoromethane (HFC-32), 1,1-difluoroethane (HFC-152a), 1,1,1-trifluoroethane (HFC-143a), 1,1,1,2-tetrafluoroethane (HFC-134a), pentafluoroethane (HFC-125), 1,1,1,3,3-pentafluoropropane (HFC-245fa), 1,1,1,3,3,3-hexafluoropropane (FC-236fa), 1,1,1,2,3,3,3-heptafluoropropane (HFC-227ea), 1,1,1,3,3-pentafluorobutane (HFC-365mfc) and 1,1,1,2,3,4,4,5,5,5-decafluoropentane (HFC-43-10mee). A hydrofluoroalkane chosen from difluoromethane, 1,1-difluoroethane, 1,1,1,3,3-pentafluoropropane, 1,1,1,2,3,3,3-heptafluoropropane and 1,1,1,3,3-pentafluorobutane is particularly preferred. A hydrofluoroalkane chosen from 1,1-difluoroethane, 1,1,1,3,3-pentafluoropropane and 1,1,1,3,3-pentafluorobutane is more particularly preferred. 1,1-Difluoroethane is very particularly preferred.

In an alternative form, the organic compound is a chlorofluorinated organic compound. Mention may in particular be made, among chlorofluorinated organic compounds, of a hydrochlorofluoroalkane chosen from chlorodifluoromethane (HCFC-22), 1,1,1-trifluoro-2,2-dichloroethane (HCFC-123), 1,1,1-trifluoro-2-chloroethane (HCFC-133a), 1-fluoro-1,1-dichloroethane (HCFC-141b) or 1,1-difluoro- 1-chloroethane (HCFC-142b) and from the chlorofluorinated intermediates in the synthesis of HFC-245fa or HFC-365mfc.

The reaction for the manufacture of the above-mentioned hydrofluoroalkanes is preferably a reaction in which a halogenated precursor of the hydrofluoroalkane is reacted with hydrogen fluoride, preferably in the liquid phase, preferably in the presence of a hydrofluorination catalyst chosen in particular from the preferred metal derivatives mentioned above. In this case, the liquid phase comprising heavy by-products subjected to evaporation in the process according to the invention, can be obtained in a stage of separation of a liquid phase reaction medium by settling. Such a procedure is particularly well suited.

Alternatively, a reaction liquid phase comprising heavy by-products withdrawn as a bleed from a catalytic liquid phase hydrofluorination reaction can be introduced directly into the evaporation stage of the process according to the invention.

In the process according to the invention, the term "heavy by-products" is understood to denote compounds which exhibit a higher boiling point than that of the reactants and solvents employed.

The content of heavy by-products in the liquid phase rich in heavy by-products is generally greater than or equal to 5% by weight. This content is often greater than or equal to 10% by weight. It is preferably greater than or equal to 20%. Generally, the content of heavy by-products in the liquid phase rich in heavy by-products is at most approximately 50% by weight.

The process according to the invention allows to form a concentrated phase comprising the bulk of the heavy by-products. Generally, the concentrated phase contains at least 80% by weight of the heavy by-products introduced into the evaporation stage. Often, the concentrated phase contains at least 90% by weight of the heavy by-products. Preferably, the concentrated phase contains at least 95% by weight of the heavy by-products. The process according to the invention allows to form a concentrated phase to which contains at least 99% by weight of the heavy by-products. The process according to the invention even allows to form a concentrated phase comprising substantially all of the heavy by-products.

In the process according to the invention, the liquid phase is generally spread over the surface by an appropriate means. The means employed for spreading is chosen according to the desired distribution of the liquid phase over the surface. It is possible, for example, to use appropriately arranged nozzles which project a stream of liquid phase directly over the surface. It is also possible to use one or more nozzles combined, for example, with a tongue which spreads the liquid projected from the nozzle over the surface. It is also possible to use a distribution ring which is preferably in the rotating state.

The liquid phase generally forms a thin film on the surface. The thin film generally exhibits a thickness of at most 50 mm. The thin film often exhibits a thickness of at most 20 mm. Preferably, this thickness is at most 15 mm. Generally, the thin film exhibits a thickness of at least 0.1 mm. The thin film often exhibits a thickness of at least 0.5 mm. Preferably, this thickness is at least 1 mm.

The geometry of the surface can, for example, be planar, cylindrical or conical. The surface is often conical or cylindrical. Preferably, it is cylindrical.

The liquid phase is brought to the surface, preferably so as to form a directed stream of liquid phase on the surface. The stream can be formed, for example, by using gravitation or by providing for a directed projection of liquid phase with respect to the surface.

The liquid phase on the surface can be in the turbulent state, it being possible for this state to be produced by known means, such as wipers which appropriately stir the thin film. It can also be in a state of laminar flow.

The pressure at which the evaporation is carried out is generally at least 0.01 bar. The pressure is often at least 0.1 bar. Preferably, it is greater than or equal to approximately 1 bar. The pressure at which the evaporation is carried out is generally at most 15 bar. The pressure is often at most 10 bar. Preferably, it is less than or equal to 5 bar. A pressure of less than or equal to approximately 3 bar is also suitable.

In the process according to the invention, the liquid phase is generally subjected to the evaporation with a flow rate of greater than or equal to 1 l/h per 1 $m^2$ of surface area. This flow rate is often greater than or equal to 5 l/h per 1 $m^2$ of surface area. Preferably, it is greater than or equal to 10 l/h per 1 $m^2$ of surface area. In the process according to the invention, the liquid phase is generally subjected to the evaporation with a flow rate of less than or equal to 500 l/h per 1 $m^2$ of surface area. This flow rate is often less than or equal to 300 l/h per 1 $m^2$ of surface area. Preferably, it is less than or equal to 100 l/h per 1 $m^2$ of surface area. Sometimes, the flow rate is less than or equal to 30 l/h per 1 $m^2$ of surface area. A flowrate of less than or equal to 20 l/h per 1 $m^2$ of surface area may also be suitable.

The surface is generally a heated surface. The temperature of the surface is often maintained at at least 20° C. The temperature is more often maintained at at least 30° C. Preferably, it is maintained at at least 50° C. The temperature of the surface is often maintained at at most 200° C. The temperature is more often maintained at at most 150° C. Preferably, it is maintained at at most 100° C. The heating of the surface may be carried out by a suitable heating means such as a heating jacket. Hot water, steam and oil can be suitably used as heat transfer fluid. Steam is preferred as the heat transfer fluid. In this case, the steam pressure is generally at least 1 bar. The steam pressure is generally at most 12 bar.

In the process according to the invention, the recovery of the concentrated phase often comprises the separation of the concentrated phase from the surface with a mechanical means for separating the concentrated phase from the surface. Mechanical means which can be used are, for example, blade rotors, scraper wipers or lobed rotors. Blade rotors with movable wiper blades give good results.

When a rotor is employed as mechanical means, the peripheral speed is generally at least 1 m/s. Preferably, the speed is at least 2 m/s. The peripheral speed is generally at most 4 m/s. Preferably, the speed is less than or equal to approximately 3 m/s.

The concentrated phase is generally separated from the surface as the concentrated phase is being formed.

Evaporators which can be used in the process according to the invention are, in particular, thin film evaporators. Such evaporators are commercially available, for example from Buss AG, GEA Canzler or Kühni. In a very particularly preferred alternative form, a wiped film evaporator is employed. In such an evaporator, a thin film of the liquid phase is evaporated on a heated surface and the concentrated phase is wiped off by a mechanical separation means.

The evaporator can be a vertical or horizontal evaporator. Use may also be made of a combination of two or more evaporators.

In a preferred form, the liquid phase comprising heavy by-products is a liquid phase enriched in heavy by-products obtained from at least a portion of the by-products from an organic reaction which is subjected to an operation for separation by settling in order to separate the liquid phase enriched in heavy by-products from a phase depleted in said heavy by-products.

The operation for separation by settling is generally carried out at a temperature below the reaction temperature for production of an organic compound. The operation for separation by settling can be carried out, for example, at ambient temperature. A temperature of less than or equal to approximately 10° C. can also be employed.

If appropriate, the duration of the operation for separation by settling is generally less than or equal to 10 hours. The duration is often less than or equal to 5 hours. Preferably, it is less than or equal to 2 hours. Generally, the duration of the operation for separation by settling is greater than or equal to 10 minutes.

Optionally, the process according to the invention additionally comprises the recycling of the vapour phase obtained in the stage of evaporation, essentially devoid of heavy by-products, to the reaction for the production of organic compounds. If appropriate, the vapour phase may be subjected to a separation step, such as, for example, a distillation prior to recycling, so as to separate or reduce the content of optionally present other impurities.

In a first preferred embodiment, the concentrated phase formed on the surface is a solid phase.

It has been found, surprisingly, that, in this embodiment, a solid phase comprising heavy by-products which is particularly well suited to environmentally-friendly destruction in an incineration plant is obtained by the process according to the invention, while retaining a high level of recycling of reactants or reaction solvents. The treatment process according to the invention does not require any addition of compounds foreign to the reaction. Consequently, the risk of contamination of the reaction medium by undesirable compounds during the recycling of reactants or reaction solvents to the reaction for the production of an organic compound is greatly reduced, indeed even nonexistent. The solid phase, which may comprise toxic products, furthermore exhibits the advantage that it can be easily handled for the purpose of its destruction, with a high degree of safety. The solid phase exhibits a high content of heavy by-products, which makes possible effective removal of the said by-products from the reaction for production of organic compounds.

The first preferred embodiment of the process according to the invention additionally may comprise a treatment for destroying the solid phase. Such a treatment can, for example, be an incineration. The process according to the invention comprising an incineration is particularly advantageous economically as it makes it possible to efficiently produce the desired organic product while providing, in an environmentally friendly way, for the destruction of the heavy by-products. If appropriate, the incineration plant can be integrated into the plant for the manufacture of an organic compound. The incineration plant is often not integrated into the plant for the manufacture of an organic compound. This specific case demonstrates an advantage of the process according to the invention, as the solid phase obtained can be handled and transported in a safe and easy manner.

The invention consequently also relates to the solid phase which can be obtained according to the process according to the invention. The solid phase is preferably in the form of a powder. The solid can also exhibit a certain content of liquids, such as, for example, residues of reactants or solvents. The liquid content is generally less than or equal to 20% by weight. Preferably, this content is less than or equal to 15% by weight.

In a second preferred embodiment, the concentrated phase is a liquid phase.

It has been found, surprisingly, that this embodiment of the process according to the invention allows to obtain a liquid phase which is sufficiently concentrated to allow for efficient removal and disposal of heavy by-products The liquid phase obtained in this embodiment of the process is also particularly well suited to environmentally-friendly destruction in an incineration plant, while retaining a high level of recycling of reactants or reaction solvents. The treatment process according to the invention does not require any addition of compounds foreign to the reaction. Consequently, the risk of contamination of the reaction medium by undesirable compounds during the recycling of reactants or reaction solvents to the reaction for the production of an organic compound is greatly reduced, indeed even nonexistent.

The concentrated liquid phase has good flow properties, which allow for easy transportation of the phase in the plant e.g. by pumping. If desired, the concentrated liquid phase can be diluted after its recovery from the surface to reduce its viscosity, for example with an appropriate organic solvent such as a chlorocarbon, in particular CCl4, or perchloroethylene. If an acid or a base is present, the concentrated liquid phase may be subjected to a neutralisation treatment, which might improve a subsequent destruction treatment, for example by incineration.

In a particular embodiment, the second preferred embodiment of the process according to the invention is applied to the treatment of by-products of a reaction for the production notably of the fluoroalkanes or chlorofluoroalkanes mentioned above, by liquid phase hydrofluorination reaction.

In this particular embodiment, the HF content in the concentrated liquid phase is generally lower than or equal to 20% by weight of the total weight of the concentrated liquid phase. Often, the HF content in the concentrated liquid phase is lower than or equal to 15% by weight of the total weight of the concentrated liquid phase. Preferably, the HF content in the concentrated liquid phase is lower than or equal to 10% by weight of the total weight of the concentrated liquid phase.

In a first particularly preferred embodiment, the first preferred embodiment or the second preferred embodiment of the process according to the invention is applied to the treatment, notably under the preferred process conditions described above, of by-products of a reaction for the production of HFC-152a by liquid phase hydrofluorination reaction, in particular in the presence of a catalyst.

In a second particularly preferred embodiment, the first preferred embodiment or the second preferred embodiment of the process according to the invention is applied to the treatment, notably under the preferred process conditions described above, of by-products of a reaction for the production of HFC-245fa by liquid phase hydrofluorination reaction, in particular in the presence of a catalyst.

In a third particularly preferred embodiment, the first preferred embodiment or the second preferred embodiment of the process according to the invention is applied to the treatment, notably under the preferred process conditions described above, of by-products of a reaction for the production of HFC-365mfc by liquid phase hydrofluorination reaction, in particular in the presence of a catalyst.

It has further been found, surprisingly, that the hydrogen fluoride used in reactions for the manufacture of a fluorinated organic compound by hydrofluorination in the liquid phase is a powerful solvent for heavy by-products, in particular for tars produced as by-products from such reactions and, if present, catalyst decomposition products.

The invention consequently also relates to the use of hydrogen fluoride as extraction solvent for heavy by-products, in particular tars and/or catalyst decomposition products, from a reaction medium for the manufacture of a fluorinated organic compound.

Consequently, in an alternative form of the treatment process according to the invention, the liquid phase comprising heavy by-products generally comprises at least 50% by weight of hydrogen fluoride. Preferably, the liquid phase comprising heavy by-products comprises at least 80% by weight of hydrogen fluoride. The liquid phase comprising heavy by-products generally comprises at most 95% by weight of hydrogen fluoride. Preferably, the liquid phase comprising heavy by-products comprises a content of hydrogen fluoride of less than or equal to approximately 90% by weight.

The invention also relates to a process for the synthesis of an organic compound comprising the process for the treatment of by-products from a reaction for the production of organic compounds as described above. The preferred organic compounds are mentioned above.

BRIEF DESCRIPTION OF DRAWING

It is the intention of FIG. 1 to illustrate in a nonlimiting way a preferred alternative form of the treatment process according to the invention applied to the treatment of by-products from a reaction for the manufacture of 1,1-difluoroethane. It is understood that this alternative form also applies to other organic compounds, in particular to the abovementioned fluorinated organic compounds and more particularly to 1,1,1,3,3-pentafluoropropane and 1,1,1,3,3-pentafluorobutane.

A liquid bleed from the reaction for the manufacture of 1,1-difluoroethane by hydrofluorination in the presence of a solvent and of a catalyst, which bleed comprises heavy by-products, is withdrawn via the pipe (2) from the reactor (1) and conveyed to the decanter (3). After separation of phases, a phase depleted in heavy by-products, essentially devoid of catalyst and of tars, is withdrawn via the pipe (4) for the purpose of being destroyed. In an alternative form, this phase is recycled via the pipe (9) to the reactor (1). A phase enriched in heavy by-products, comprising hydrogen fluoride, tars and catalyst decomposition products, is introduced via the pipe (5) into a wiped film evaporator (6). A gas phase comprising hydrogen fluoride essentially devoid of tars and of catalyst decomposition products is withdrawn via the pipe (7) and recycled to the reactor (1). A powder comprising tars and catalyst decomposition products is recovered at the bottom (8) of the evaporator (6) for the purpose of being destroyed.

The examples given below are intended to illustrate the invention without however, limiting it.

EXAMPLE 1

An analysis was carried out of a phase enriched in heavy by-products, obtained by separation by settling at 20° C. for 1 hour starting from a liquid reaction medium comprising heavy by-products, in which medium a hydrofluorination of vinyl chloride has been carried out in the presence of tin tetrachloride to manufacture 1,1-difluoroethane, in the presence of a solvent. The reaction medium comprised 12% by weight of hydrogen fluoride and 2.3% by weight of heavy by-products, including 1.2% by weight of tin and 1.1% by weight of tars. The phase enriched in heavy by-products was homogeneous. It was composed essentially of hydrogen fluoride exhibiting a content of heavy by-products of 17.2% by weight, including 3.2% by weight of tin.

EXAMPLE 2

118 liters of an inorganic phase in accordance with Example 1 were introduced into a vertical wiped film evaporator manufactured by SMS (Buss-Lewa) of Sambay T 100 type, exhibiting the following characteristics:
Cylindrical internal exchange surface area: 0.3 m²
Material: Stainless steel 1.4571
Double packing with perchloroethylene barrier fluid
Mechanical separation means: Rotor comprising 7 components of 3 movable wiper blades.

The rotational speed was 480 revolutions/minute. The maximum peripheral speed was 3 m/s. The feed flow rate was adjusted to approximately 4.7 l/h. The top temperature of the evaporator was approximately 30° C. A gas phase composed essentially of hydrogen fluoride essentially devoid of tin and of tars was withdrawn at the top of the evaporator. This phase was suitable for recycling in the hydrofluorination reaction. 13.5 kg of a solid phase comprising tars, tin derivatives and adsorbed hydrogen fluoride were recovered at the bottom of the evaporator. Drying in air was carried out for 24 h. The fine powder obtained exhibited a liquid content of approximately 11.5% by weight. The tin content was 17.3% by weight with respect to the total weight of the solid phase.

This solid phase was suitable for destruction by incineration. It could be easily handled (taking into account the presence of adsorbed hydrogen fluoride). The solid phase was heated for 6 hours at 120° C. The solid obtained comprised 62.6% by weight of tars and 37.4% by weight of tin halide.

EXAMPLE 3

A bleed from a catalytic liquid phase hydrofluorination reaction for the manufacture of HFC-365mfc from 1,1,1,3,3-pentachlorobutane was directly introduced into the evaporator of example 2. The bleed contained 75% wt. of HF, HPC-365mfc and chlorofluorinated intermediates of HFC-365mfc and 25% wt of heavy by-products, notably metal salt catalyst decomposition products and tar.

The treatment was carried out under the following conditions:

The rotational speed was 480 revolutions/minute. The maximum peripheral speed was 3 m/s. The feed flow rate was adjusted to approximately 20 l/h. The top temperature of the evaporator was approximately. 50° C. A gas phase composed essentially of hydrogen fluoride essentially devoid of catalyst and of tars was withdrawn at the top of the evaporator. This phase was subjected to a distillation and then recycled in the hydrofluorination reaction. 2 Kg/h of a concentrated liquid phase was recovered at the bottom of the evaporator. This phase contained more than 95% by weight of the heavy by-products which had been contained in the bleed. Its HF content was 3% by weight. The concentrated liquid phase was suitable to be pumped and could be destroyed by incineration after the neutralisation of HF.

The invention claimed is:

1. A process for the treatment of by-products from a reaction for the production of a halogenated organic compounds comprising a stage of evaporation of a liquid phase comprising heavy by-products on a surface in order to form a concentrated phase comprising the bulk of the heavy by-products and a vapour phase essentially devoid of heavy by-products, and a stage of recovery of the concentrated phase from the surface wherein said heavy by-products denote compounds which exhibit a higher boiling point than that of the reactants and solvents.

2. The process according to claim 1, in which the liquid phase forms a thin film on the surface exhibiting a thickness of at most 50 mm.

3. The process according to claim 1, in which the liquid phase is brought to the surface so as to form a directed stream of liquid phase on the surface.

4. The process according to claim 1, in which the liquid phase on the surface is in the turbulent state.

5. The process according to claim 1, in which the pressure at which the evaporation is carried out is from 0.01 to 15 bar.

6. The process according to claim 1, in which the liquid phase is subjected to the evaporation with a flow rate of 1 to 500 l/h per 1 m² of surface area.

7. The process according to claim 1, in which the surface is a heated surface.

8. The process according to claim 1, in which the recovery of the concentrated phase comprises a separation of the concentrated phase from the surface with a mechanical means.

9. The process according to claim 1, carried out in a wiped film evaporator.

10. The process according to claim 8, in which the concentrated phase is separated from the surface as the concentrated phase is being formed.

11. The process according to claim 1, wherein the concentrated phase is a solid phase.

12. The process according to claim 1, wherein the concentrated phase is a liquid phase.

13. The process according to claim 1, in which the liquid phase comprising heavy by-products is a liquid phase enriched in heavy by-products obtained from at least a portion of the by-products from an organic reaction which is subjected to an operation for separation by settling in order to separate the liquid phase enriched In heavy by-products from a phase depleted in said heavy by-products.

14. The process according to claim 1, additionally comprising the recycling of the vapour phase, essentially devoid of heavy by-products, to the reaction for the production of organic compounds.

15. The process according to claim 1, in which the halogenated organic compound is a hydrofluoroalkane chosen from difluoromethane (HFC-32), 1,1-difluoroethane (HFC-152a), 1,1,1-trifluoroethane (HFC-143a), 1,1,1,2-tetrafluoroethane (HFC-134a), pentafluoroethane (HFC-125), 1,1,1,3,3-pentafluoropropane (HFC-245fa), 1,1,1,3,3,3-hexafluoropropane (HFC-236fa), 1,1,1,2,3,3,3-heptafluoropropane (HFC-227ea), 1,1,1,3,3-pentafluorobutane (HFC-365mfc) and 1,1,1,2,3,4,4,5,5,5-decafluoropentane (HIFC-43-10mee) or a hydrochlorofluoroalkane chosen from chlorodifluoromethane (HCFC-22), 1,1,1-trifluoro-2,2-dichloroethane (HCFC-123), 1,1,1-trifluoro-2-chloroethane (HCFC-133a), 1-fluoro-1,1-dichloroethane (HCFC-141b) or 1,1-difluoro-1-chloroethane (HCFC-142b) and from the chlorofluorinated intermediates in the synthesis of HFC-245fa or HFC-365mfc.

16. The process according to claim 15, in which the halogenated organic compound is 1,1-difluoroethane (HFC-152a).

17. The process according to claim 15, in which the halogenated organic compound is 1,1,1,3,3-pentafluorobutane (HFC-365mfc).

18. The process far the synthesis of an organic compound, comprising the process for the treatment of by-products from a reaction for the production of organic compounds according to claim 1.

19. A method for eliminating heavy by-products comprising use of hydrogen fluoride as extraction solvent for said heavy by-products wherein the heavy by-products are tars and/or catalyst decomposition products from a reaction medium for the manufacture of fluorinated organic compounds.

* * * * *